United States Patent [19]

Uffer

[11] 4,018,684
[45] Apr. 19, 1977

[54] ELECTRONIC AUTOCLAVE TIMING CIRCUIT FOR KIDNEY DIALYSIS APPARATUS

[75] Inventor: Michael B. Uffer, Baltimore, Md.

[73] Assignee: Baxter Travenol Laboratories, Inc., Deerfield, Ill.

[22] Filed: July 31, 1975

[21] Appl. No.: 600,594

[52] U.S. Cl. ............................ 210/140; 210/321 B; 235/92 R; 23/253 A

[51] Int. Cl.² ....................................... B01D 31/00

[58] Field of Search .................. 235/92; 328/3, 69; 210/321 K, 140; 23/253 A, 290; 21/93–98; 134/22 R, 22 C, 24

[56] References Cited
UNITED STATES PATENTS

| | | | |
|---|---|---|---|
| 3,454,352 | 7/1969 | Lamboy et al. ................ | 23/290 X |
| 3,571,563 | 3/1971 | Shulz ............................. | 23/290 X |
| 3,744,636 | 7/1973 | Commarmot .................. | 210/321 K X |

*Primary Examiner*—Frank A. Spear, Jr.
*Assistant Examiner*—Ferris H. Lander
*Attorney, Agent, or Firm*—Richard G. Kinney; H. Karl Saalbach; Henry W. Collins

[57] ABSTRACT

Disclosed herein is an improved electronic control system for the autoclaving sequence of a kidney dialysis machine, during which water is circulated at high temperature and pressure to clean and sterilize the machine. The circuit ensures that the machine will be autoclaved for a minimum period of time, such as 20 minutes, measured only while the temperature is above a minimum, such as 120° centigrade. The circuit will remember the time of autoclaving previous to a power interruption, and will continue to time the autoclaving function only when the temperature has again exceeded the set minimum. Once an autoclaving sequence is initiated, the circuit prevents normal use of the machine until the sequence is completed. During the autoclave timing sequence, the kidney by-pass solenoid is energized and de-energized on a 50% duty cycle to make sure all flow paths in the machine are cleaned and sterilized.

7 Claims, 1 Drawing Figure

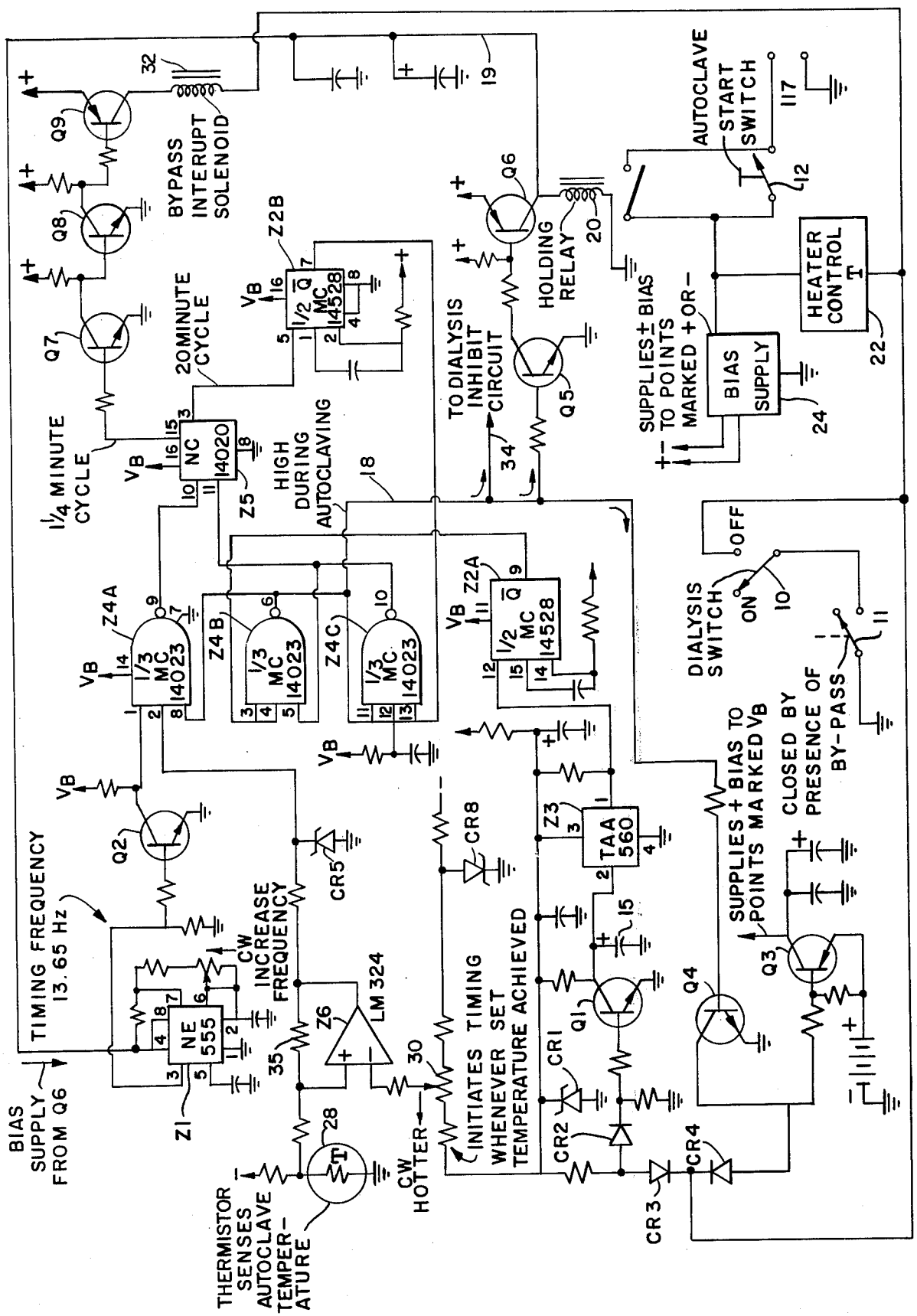

ELECTRONIC AUTOCLAVE TIMING CIRCUIT FOR KIDNEY DIALYSIS APPARATUS

BACKGROUND OF THE INVENTION

In recent years victims of renal disease have increasingly been assisted by use of the blood cleansing ability of kidney dialysis machines, which substitute for non-functioning kidneys. A small portion of the victim's blood is made to circulate, outside the body, through a fluid loop which is separated from a saline solution by an exceedingly thin membrane. The membrane is permeable to smaller molecules, such as urea, and impermeable to larger molecules, such as colloids. Accordingly, many of the poisons in the blood can be dialyzed across the membrane and discharged into the saline solution, thereby reducing the poison load in the bloodstream, without excessive loss of proteins, etc., from the patient's blood.

A typical example of a kidney dialysis machine is that of U.S. Pat. No. 3,878,095 for a DIALYSIS APPARATUS, issued to J. D. Frasier and A. Stevenson, Apr. 15, 1975. It will be seen from that disclosure that such a machine is complex and expensive.

In view of the high cost of kidney dialysis machines, it is the usual practice to use one machine for a number of patients in turn, often around the clock.

Between uses, the machine must be cleaned and also sterilized. This is usually done with sterilizing solutions, such as formaldehyde or chlorine, while a temporary shunt is connected as a substitute for the single-use dialysis membrane. For example, in the Frasier and Stevens patent a shunt 57 (labeled 56 in the drawing) is substituted for the Kiil dialysis member K, as explained in the patent, at column 10, lines 39 to 43. Hot water has also been used to sterilize kidney dialysis machines, as shown by the patents to A. U. Austin and R. S. Patch, U.S. Pat. Nos. 3,352,779, issued Nov. 14, 1967, and E. J. Serfass, J. E. Martin and W. E. Wilson, 3,441,136, issued Apr. 29, 1969.

BRIEF SUMMARY

The present invention relates to an electric heating control system which can be adapted for use, for example, as an autoclaving means for the DIALYSIS APPARATUS of the U.S. Pat. No. 3,878,095, previously referred to. Proper safeguards are provided for the safety of the patient. Autoclaving cannot commence while the patient is connected to the machine. Furthermore, once the autoclaving sequence has been instituted, the timing thereof cannot be cut short. Dispite any temporary interruptions of the main power supply, the equipment must be maintained above a minimum temperature, such as 120° centigrade, for a set total time, such as 20 minutes, before the circuit will recognize that autoclaving is complete. If the power interruption is lengthy, the equipment will cool below 120° C., and timing to measure the twenty minute period does not commence when power is restored, but is delayed until the temperature again exceeds 120° C.

Furthermore, in order to clean and sterilize all of the passages in the equipment, during the 20 minute autoclaving cycle, the kidney by-pass solenoid is periodically energized on and off, so as to circulate fluid at autoclaving temperature through all the fluid pathways in the machine.

DETAILED DESCRIPTION

The sole FIGURE of drawing is a schematic diagram of the invention.

Before an autoclave cycle can be initiated, the dialysis on-off switch of the dialyzer apparatus must be "off," to ensure that a patient is not connected. This switch is ganged to the switch 10, shown as being in the "on" position, in which it is open-circuited. Furthermore, the Kiil dialysis unit must have been removed from the machine and a by-pass shunt, such as that of the Frasier and Stevens U.S. Pat. No. 3,878,095, must have been substituted for the Kiil dialyzer. When such substitution is made, a switch 11 is automatically closed by an interlock on the by-pass shunt.

When switches 10 and 11 are both in the closed position, the junction of diodes CR3 and CR4 is at ground potential. This strongly forward biases the emitter of Q3, and as a result positive battery potential is applied from the collector of Q3 to all the points labeled $V_B$, thereby energizing the transistor Q2 and the integrated CMOS circuits Z2A, Z2B, Z4A, Z4B, Z4C and Z5.

The other transistors and integrated circuits shown are supplied with bias obtained from the AC power lines, and may therefore be subject to power interruption, but during such power interruption, the internal battery, which is kept on float, will maintain energized certain parts of the circuit, so that certain information stored therein is not lost.

The autoclave actuating switch 12 is a push button type which must be held down for a period of 25 seconds to initiate autoclaving. When the autoclave actuating switch 12 is actuated, positive bias is applied to the collector of Q1 from the bias supply 24. The transistor Q1 is in the nonconducting condition since the "off" dialysis switch 10 and the closed by-pass presence detecting switch 11 have effectively grounded the junction of diodes CR3 and CR2, and therefore have also grounded the base of Q1. (If the by-pass were not present or if the dialysis switch were "on," the junction of diode CR3 and CR2 would rise positively towards the voltage set by voltage regulator diode CR1, and the resulting positive voltage on the base of Q1 would effectively short circuit Q1.) Since Q1 is open, the capacitor 15 slowly charges positively while the switch 12 is depressed. After about 25 seconds, long enough to ensure a purposeful diligence on the part of the operator, the bias on capacitor 15 is high enough to trip the Schmidt trigger circuit Z3. This will then trigger the one-shot Z2A, which then sets the output of logic gate Z4B to the high level. When Z4B goes high, the high output is carried by conductor 18 to Q5. Q5 turns on, which turns Q6 on.

The turning on of Q6 has several consequences. It raises the potential of the line 19, so that positive bias is supplied to oscillator Z1, which thereupon starts generating a clocking frequency of 13.65 hertz. It also pulls up the holding relay 20, the contacts of which are in shunt with the contacts of autoclave switch 12. If the push button of the autoclave switch 12 is released before the expiration of 25 seconds, the autoclave heater control 22 (the heater itself has not yet achieved a high temperature because of its thermal inertia) and the bias supply 24 are de-energized. If the push button of autoclave switch 12 is released after 25 seconds, the holding circuit of holding relay 20 continues to maintain the energization of autoclave heater control 22 and bias supply 24.

It will be noted, however, that if, after the holding circuit is established, either the dialysis switch 10 is turned to "on" or the by-pass shunt is removed, thereby opening switch 11, the autoclave heater control 22 is de-energized, so that no heating takes place. However, under this circumstance, the base of transistor Q3 continues to be grounded by the action of transistor Q4, because the potential of conductor 18 continues to remain high. Thus, the CMOS logic gate Z4B, and other active circuits biased through transistor Q3 from the battery are not de-energized, but continue to function.

If there is an interruption in the AC power supply and line 18 is high, the holding relay 20 drops out because the holding relay is powered through Q6 from the bias supply 24, so that when AC power is restored, the autoclave heater control 22 is not reenergized. If the autoclave cycle has not been completed, line 18 continues to remain high, so that when the AC power supply is restored, a momentary depression of autoclave switch 12 will reestablish autoclaving. Holding relay 20 is slow to drop out, so the equipment will be unaffected by very short interruptions of AC power.

The autoclave heater is provided with a thermistor 28 which controls an operational amplifier Z6. As the thermistor 28 heats up, the voltage on the positive input of the operational amplifier increases. When it reaches a value determined by the position of the tap on potentiometer 30, the output of Z6 goes high. As will be seen shortly, the position of the tap of potentiometer 30 determines how hot the autoclave heater must get before timing commences. At lesser temperatures, the circuit operates with a time-out function.

The feedback resistor 35 for operational amplifier Z6 operates to produce hysteresis between the timing activate temperature and the timing deactivate temperature. This is desirable so that minute fluctuations of temperature do not result in cyclic changes of the timing function.

When the desired autoclave temperature has been reached and the output of operational amplifier Z6 is high, then one output (No. 2) of Z4A is high because the temperature is over the set-point, a second (No. 8) is high because Z4B has gone high, and the third input (No. 1) is clocking high and low. Therefore, the output of Z4A is now clocking the input of Z5, a 14 bit binary counter, at the rate of 13.65 Hz.

Every 1024 counts (or 1¼ minutes) the output of Z5 at terminal 15 changes state, and through the chain Q7, Q8 and Q9 energizes or de-energizes the kidney by-pass solenoid 32. Thus, the hot fluids are circulated through the alternative fluid passageways, whose sterility is critical to the next patient.

After 16384 counts (or 20 minutes) the output of Z5 at terminal 3 goes negative, and this transition fires one-shot Z2B, which thereupon resets the R-S flip-flop formed by Z4B and Z4C. Since Z4B has reversed its output, line 18 is no longer high, so that transistors Q5 and Q6 turn off.

The de-energization of transistor Q6 has several consequences. It removes bias potential from the conductor 19, thereby de-energizing oscillator Z1, which no longer generates a clocking frequency. It permits the holding relay 20 to drop out, thereby interrupting the power for the autoclave heater control 22 at autoclave switch 12, now open. The autoclave timing interval is now over.

Had the power failed before the autoclaving interval was finished, the oscillator would lose its bias supply and stop counting, but the battery would preserve the count in the counter Z5 and also keep Z4B in the high state. As soon as the output of power is restored, the autoclave timer will resume timing where it left off. If the temperature has dropped below minimum autoclave temperature, the timing will not resume until minimum temperature is again reached.

While the machine is in the autoclave mode, the conductor 18 remains high until the binary counter Z5 changes its output at terminal 3. Use is made of this to inhibit the operation of the machine in the dialysis mode by extending conductor 18 over lead 34 to a dialysis control portion of the machine, not shown. For example, lead 34 can control a relay which cuts off energizing power to the dialysis portion of the machine.

I claim:

1. In a kidney dialysis machine, having means to substitute a by-pass shunt for the dialysis unit, and having electric heating means to raise the machine temperature to a desired autoclaving temperature, said by-pass shunt and said electric heating means being used for autoclaving said machine between patient uses, the improvement comprising:
   manual means to initiate energization of said electric heating means;
   automatic means to continue energization of said electric heating means;
   means to sense the attainment of the desired autoclaving temperature by said electric heating means;
   electronic timing means for timing the duration of a desired autoclaving period;
   said electronic timing means having logic gate means, responsive to said attainment, for suspending said timing while or whenever said desired autoclaving temperature has not been achieved;
   means responsive to the electronic timing means to terminate energization of sid electric heater by said automatic means when the electronic timing means has measured the desired duration;
   and means responsive to the absence of said by-pass shunt to prevent said automatic means from continuing energization of said electric heating means.

2. The improvement of claim 1 in combination with:
   retarding means for preventing the said initiation of continuation until after said manual means has been actuated for a predetermined time.

3. The improvement of claim 2 in which the said predetermined time is of such length as to require purposeful prolonged actuation of said manual means, precluding momentary actuation.

4. The improvement of claim 3 in which said predetermined time is approximately 25 seconds.

5. The improvement of claim 1 in combination with:
   means supplying from said electronic timing means a pulsing signal of periodicity much shorter than the said desired autoclaving period;
   means for periodically shifting the flow of fluids in said kidney dialysis machine between all alternative fluid flow paths, in response to said pulsing signal;
   whereby all critical fluid pathways in said kidney dialysis machine are autoclaved.

6. In a kidney dialysis machine:

electric heating means to raise the machine temperature to a desired autoclaving temperature;

control means to maintain said autoclaving temperature for a desired total elapsed interval with time out means effective during lapses in said desired autoclaving temperature; and means for periodically shifting the flow of fluids in said kidney dialysis machine between all critical alternative fluid flow paths during said desired total elapsed interval;

whereby all critical fluid flow pathways in said kidney dialysis machine are autoclaved.

7. In a kidney dialysis machine, means for autoclaving said machine between patient uses, said means comprising:

electric heating means to raise the temperature of the fluid passageways to an autoclaving temperature;

temperature sensing means to sense the attainment of autoclaving temperature;

timing means for measuring a predetermined time interval;

means for inhibiting the said timing means at all times except when the temperature sensing means indicates the attainment of autoclaving temperature;

manually actuatable means for energizing the said electric heating means;

automatically actuatable means for de-energizing the electric heating means in response to the measurement by said timing means of said predetermined time interval; and means, responsive to the measurement by said timing means of an elapsed period less than said predetermined time interval, preventing operation of said kidney dialysis machine with a patient.

* * * * *